United States Patent
Matsumoto et al.

(10) Patent No.: US 6,528,648 B2
(45) Date of Patent: Mar. 4, 2003

(54) DETECTING REAGENT FOR DOUBLE-STRANDED NUCLEIC ACID AND DOUBLE-STRANDED NUCLEIC ACID DETECTING METHOD

(75) Inventors: Kazuko Matsumoto, Tokyo (JP); Takahiko Nojima, Tokyo (JP); Hideo Tashiro, Wako (JP); Yasumitsu Kondoh, Wako (JP); Shigeori Takenaka, Koga (JP)

(73) Assignee: Waseda University and Riken (JP)

(*) Notice: Subject to any disclaimer, the term of this patent is extended or adjusted under 35 U.S.C. 154(b) by 0 days.

(21) Appl. No.: 10/012,211

(22) Filed: Dec. 5, 2001

(65) Prior Publication Data

US 2002/0150929 A1 Oct. 17, 2002

(30) Foreign Application Priority Data

Dec. 8, 2000 (JP) ......................... 2000-374626

(51) Int. Cl.[7] .................. C07D 291/00; C07D 279/00; C07D 265/00; C07D 251/00; C12Q 1/68
(52) U.S. Cl. ................. 544/2; 544/4; 544/14; 544/63; 544/215; 435/6; 536/22.1; 536/23.1; 536/26.6
(58) Field of Search ............... 435/6; 536/22.1, 536/23.1, 26.6; 544/2, 4, 14, 63, 215

(56) References Cited

U.S. PATENT DOCUMENTS 6,294,670 B1 * 9/2001 Takenaka .................... 544/225
6,339,172 B1 * 1/2002 Matsui et al. ............... 562/828

OTHER PUBLICATIONS

Bunseki Kagaku. *Synthetic Threading Intercalators As A New Analytical Probe For Nucleic Acid and Gene Detection.* The Japan Society For Analytical Chemistry, vol. 48, No. 12, pp. 1095–1105 (1999).

* cited by examiner

*Primary Examiner*—Jezia Riley
(74) *Attorney, Agent, or Firm*—Ohlandt, Greeley, Ruggiero & Perle, L.L.P.

(57) ABSTRACT

The present invention provides a novel detecting reagent for double-stranded nucleic acid, and a method of using it to detect double-stranded nucleic acid formed by hybridization with a probe, with absolutely no labeling of the target nucleic acid.

The detecting reagent for double-stranded nucleic acid of the invention is characterized by comprising, in the same molecule, a naphthalenediimide group which is intercalatable into double-stranded nucleic acid and a β-diketone group capable of forming a lanthanoid metal complex.

3 Claims, 2 Drawing Sheets

■ Hybridization of complementary sequence target DNA
☐ Using non-complementary sequence target DNA

DETECTING REAGENT FOR DOUBLE-STRANDED NUCLEIC ACID AND DOUBLE-STRANDED NUCLEIC ACID DETECTING METHOD

FIELD OF THE INVENTION

The present invention relates to a novel detecting reagent for double-stranded nucleic acid and to a double-stranded nucleic acid detecting method employing it.

BACKGROUND OF THE INVENTION

Gene expression analysis experiments using microarrays have conventionally employed the following experimental procedure. Specifically, (1) a probe nucleic acid is immobilized on a substrate, (2) two different biospecimens, for example, cells at different cell cycle stages, or an mRNA mixture prepared from healthy human tissue and patient tissue or a cDNA mixture prepared by reverse transcription therefrom, are labeled with dyes having different fluorescent properties to prepare target nucleic acid, and (3) the target is competitively hybridized to the probe and then washed, and the relative fluorescent intensities of the two different dyes bonded to the remaining target are measured.

The methods currently used for immobilization of the probe nucleic acid are largely of two types. That is, (1) methods in which a lithographic technique is used to polymerize the probe nucleic acid monomers onto the substrate one residue at a time, and (2) methods in which the specimen-derived nucleic acid sample, or nucleic acid prepared therefrom by PCR or reverse transcription, is spotted.

Several methods are used for labeling of the target nucleic acid, as well. These include (1) methods in which nucleotide substitution reaction is utilized for insertion of labeled nucleotides into the specimen-derived mRNA mixture, and (2) methods in which a labeled substrate is used for the specimen-derived mRNA mixture and the labeled nucleic acid is amplified by reverse transcription and PCR.

However, labeling by such methods can affect the expressed gene abundance ratio in the sample, and this can constitute a problem in terms of the detecting precision or detection sensitivity for specimens with a low abundance ratio in the measuring sample.

It has therefore been strongly desired to develop a method of detecting and quantifying double-stranded nucleic acid formed by hybridization with a probe, without carrying out any labeling of the target nucleic acid.

SUMMARY OF THE INVENTION

It is an object of the present invention to provide a novel detecting reagent for double-stranded nucleic acid which requires absolutely no labeling of the target nucleic acid, as well as a double-stranded nucleic acid detecting method employing it.

As a result of diligent research directed toward solving the aforementioned problems associated with the prior art, the present inventors have completed the present invention upon successfully discovering a detecting reagent which (1) intercalates only with double-stranded nucleic acid formed by target nucleic acid, without any labeling, and (2) has a function allowing high-precision, high-sensitivity fluorescent analysis.

Specifically, the detecting reagent for double-stranded nucleic acid according to the invention is characterized by comprising, in the same molecule, a naphthalenediimide skeleton as a group which is intercalatable into double-stranded nucleic acid, and a β-diketone group having a specific structure rendering it capable of forming a lanthanoid metal complex.

More specifically, the detecting reagent for double-stranded nucleic acid according to the invention is characterized by having a chemical structure represented by the following formula (1) or (2).

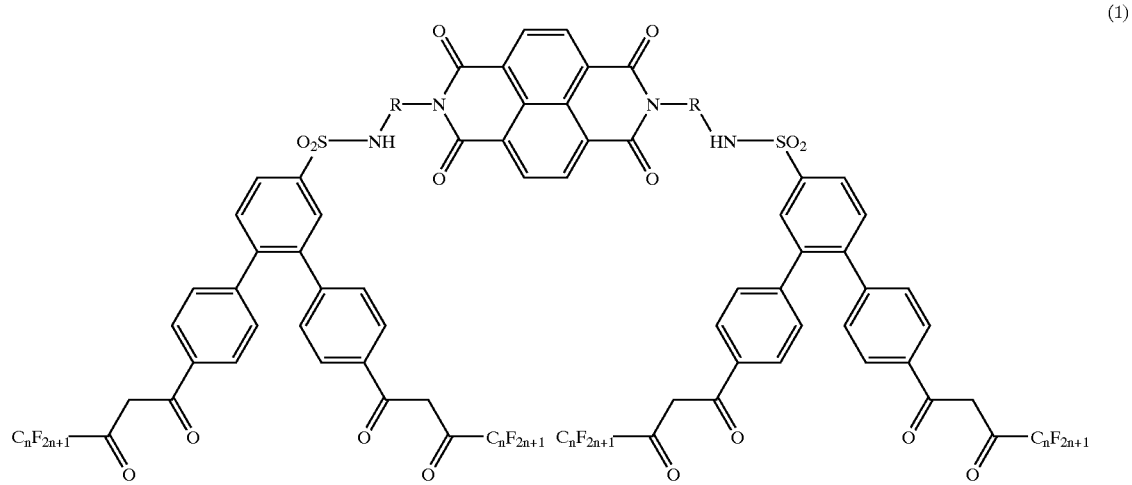

(1)

-continued (2)

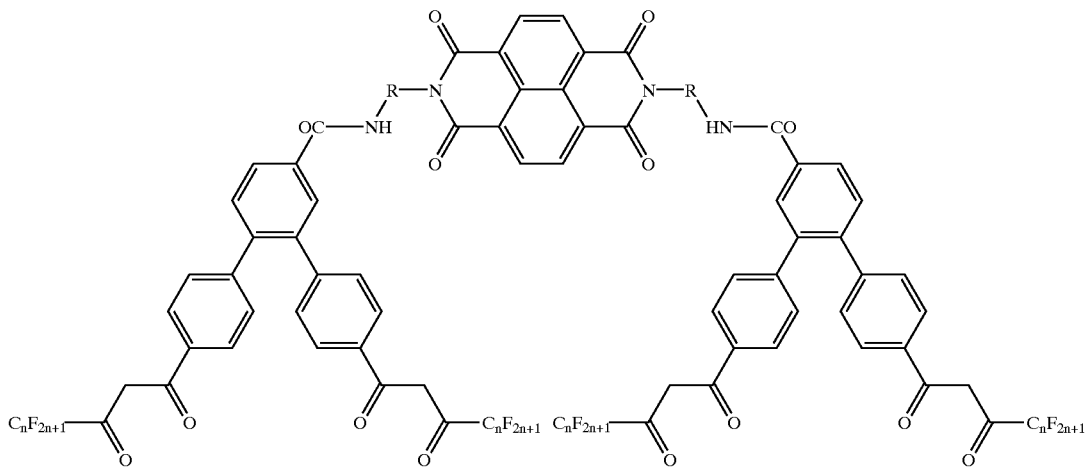

where R is a linker represented by $-C_mH_{2m}N(R')C_nH_{2n}-$, R' is an alkyl group, and m and n are each integers of 1–10.

The detecting reagent for double-stranded nucleic acid according to the invention also encompasses those comprising a fluorescent lanthanoid metal complex wherein a lanthanoid metal is coordinated in the β-diketone group.

The double-stranded nucleic acid detecting method of the invention is characterized by forming double-stranded nucleic acid with target nucleic acid and a probe, intercalating into the double-stranded nucleic acid a detecting reagent for double-stranded nucleic acid comprising a lanthanoid metal complex according to the invention, and measuring the fluorescence of the lanthanoid metal complex to detect and quantify the double-stranded nucleic acid. The invention also includes a method of quantifying the molecular length and number of molecules of the target nucleic acid by this detecting method, and a method of determining the base sequence of the nucleic acid. The invention still further includes this detecting reagent for double-stranded nucleic acid which is bonded to molecules in a specimen such as various other organic compounds, nucleic acids, oxygen, antigens, antibodies, etc., as well as a method of detecting nucleic acid and proteins using it.

The present invention will be explained hereunder in further detail by way of examples, with the understanding that they are only intended to be illustrative and not restrictive on the invention.

Biotin-labeled probe DNA was bound to an avidin-coated plate, target DNA having a sequence complementary to the probe DNA was added, and the plate was allowed to stand at room temperature for one hour. First and second washes were performed with 1×SSC. The same experiment was carried out for a sample with no probe DNA added to the plate (no probe) and a sample where the probe DNA and target DNA were non-complementary (mismatch).

Figure 1:
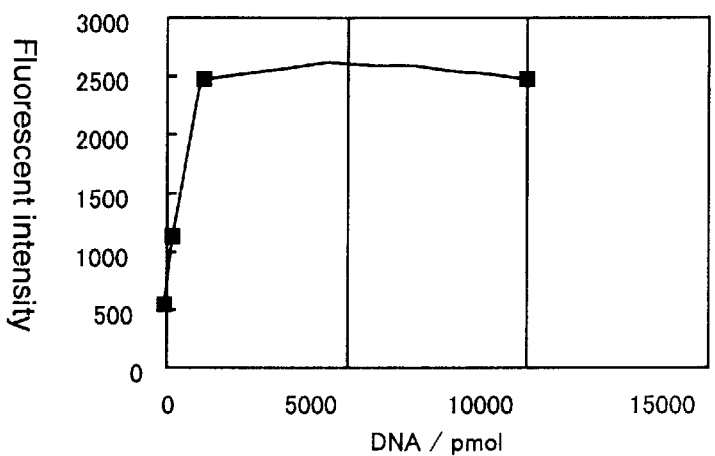
FIG. 1 shows binding of biotin-labeled DNA to an avidin-coated plate.
Figure 2:
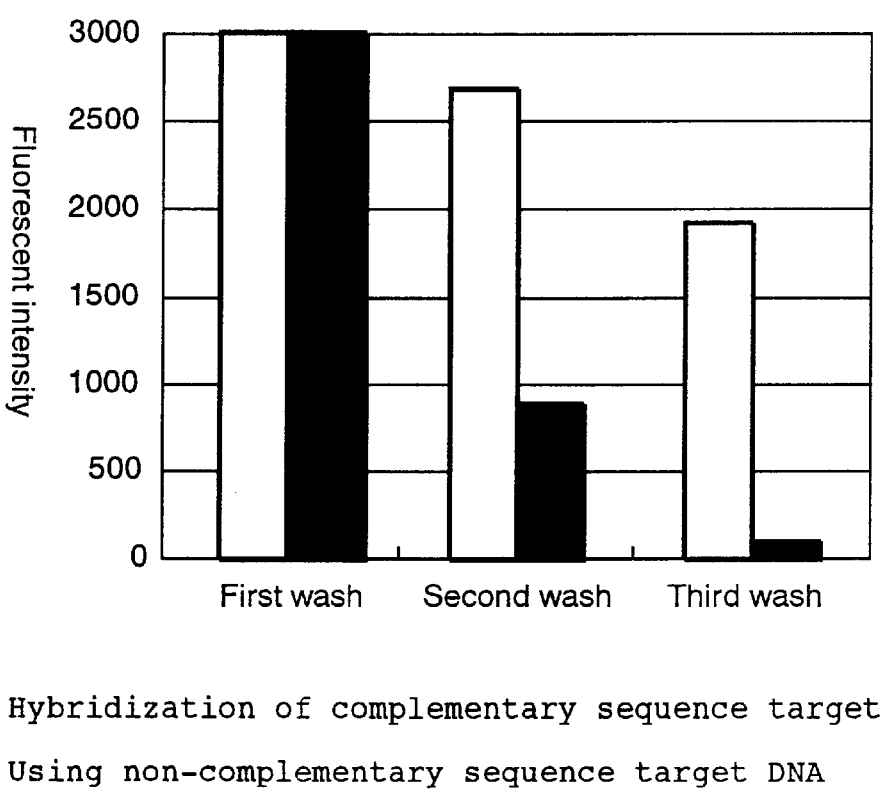
FIG. 2 is a bar graph showing fluorescent intensity measurement data for complementary DNA hybridization to biotin-labeled DNA immobilized on an assay plate.
Figure 3:
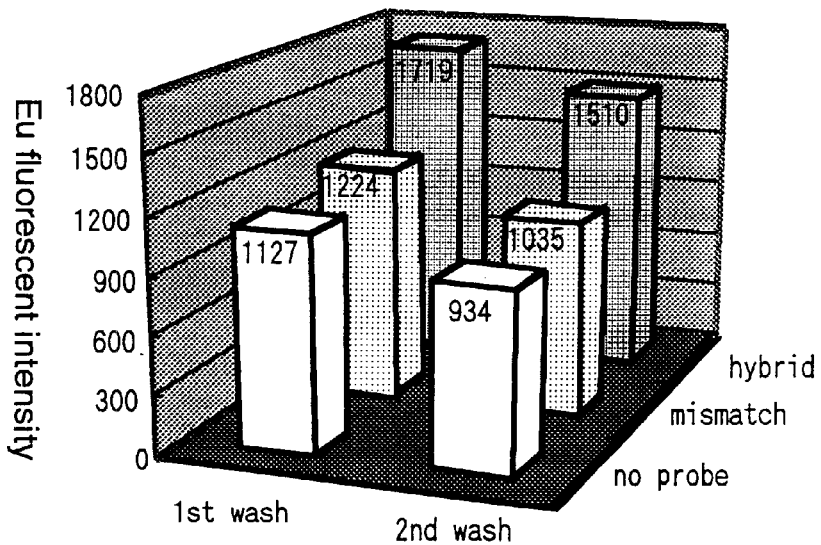
FIG. 3 is a three-dimensional bar graph showing the hybridization measurement results based on europium fluorescence.
Figure 4:
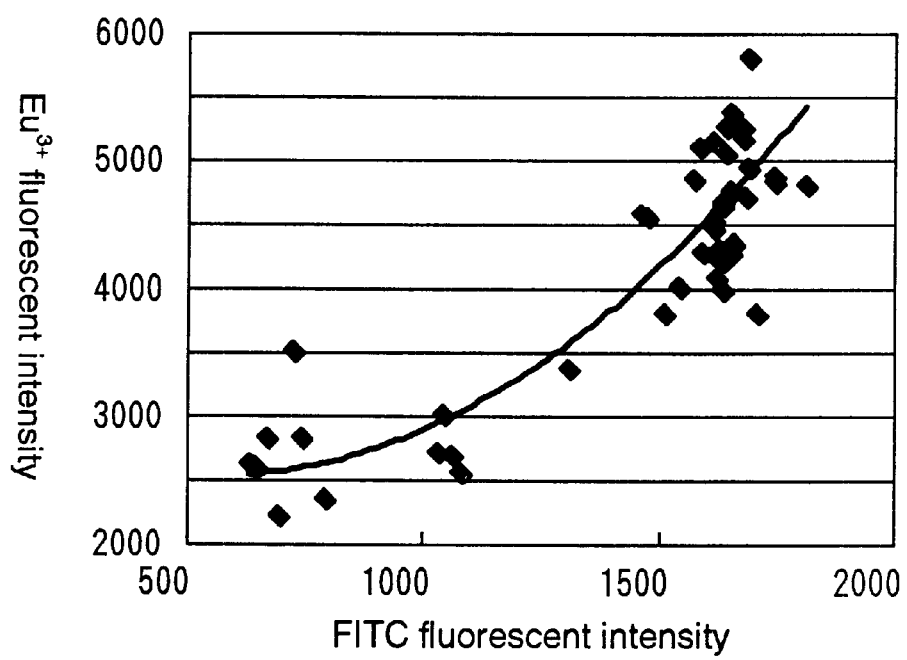

FIG. 4 is a graph showing the relationship between number of double-stranded DNA molecules immobilized on a plate and the intercalated complex fluorescent intensity.

DNA molecules were prepared by PCR using two different primers, a biotin-labeled primer and an FITC-labeled primer. The chain length was 149 bp. The DNA was immobilized on an avidin-coated plate and thoroughly washed, after which a europium complex intercalator was added and washing was performed twice. The FITC and europium fluorescent intensities were measured after washing.

DETAILED DESCRIPTION OF THE INVENTION

There are no particular restrictions on the double-stranded nucleic acid to be detected according to the invention. It may be double-stranded nucleic acid formed in solution or double-stranded nucleic acid formed on a solid phase. Normally, the probe nucleic acid is immobilized on a specific substrate to allow hybridization with a sample containing the target nucleic acid to be detected. The probe nucleic acid immobilized on the solid phase is also not particularly restricted, and for example, there may be mentioned single-stranded DNA, RNA and PNA (peptide nucleic acid) containing base sequences that can hybridize with the target nucleic acid. Single-stranded DNA and RNA may be mentioned for the target nucleic acid. No restrictions at all are placed on their origin.

The detecting reagent of the invention is characterized by comprising a group in the molecule that intercalates into double-stranded nucleic acid (throughout the present specification, this will sometimes be referred to as "intercalator"), and publicly known groups with a known function may be selected. The reagent of the invention preferably comprises a naphthalenediimide skeleton.

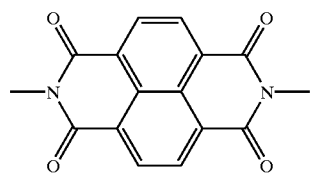

The detecting reagent of the invention is also characterized by having in the molecule a group that forms a complex with a lanthanoid metal, and there may be selected a publicly known group with a known function. According to the invention, formation of the complex with a β-diketone skeleton is preferred. For formation of a stable complex, the β-diketone selected for the detecting reagent of the invention preferably has a structure capable of coordination with 8 oxygen atoms in one molecule. More specifically, there may be mentioned the β-diketone represented by the following formula, having fluoroalkyl groups and biphenyl groups as substituents (such β-diketones will be referred to as BHHCT).

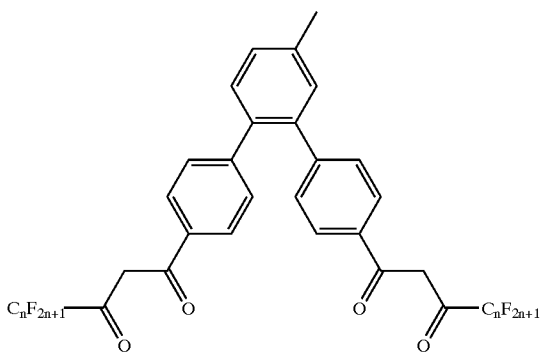

wherein n is an integer of 1–10.

These two different groups are preferably covalently bonded, and any of various publicly known covalent bonding reactions may be selected. Specifically, the following bonds may be mentioned.

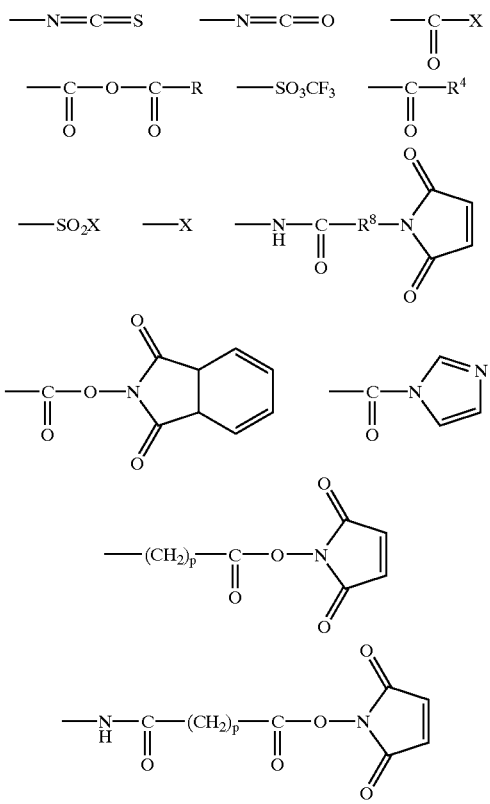

wherein X is selected from among halide atoms, —$OSO_3CH_3$, —$OSO_2F$, —$OSO_2CF_3$, —$SO_2C_4F_9$ and —$OSO_2C_6H_4$—$CH_3$, $R^A$ is selected from among alkyl, alkenyl, aryl and aralkyl groups, $R^B$ is selected from among alkylene, arylene and aralkylene groups, p is an integer of 0–5 and q is an integer of 2–10.

The lanthanoid metal ion used for the invention may be, for example, an ion of europium (Eu), samarium (Sm), terbium (Tb), dysprosium (Dy) or the like, which may be appropriately selected depending on the fluorescent properties.

There are no particular restrictions on the method of synthesizing the detecting reagent of the invention, and it may be obtained by covalent bonding between the groups having the functions described above, with bonding groups of the appropriate type and length.

More specifically, it is preferably carried out by the following four steps. Each of these steps will be described separately.

Step I

N,N-bis(3-aminopropyl)methylamine is dissolved in 1,4-dioxane, a solution of S-tert-butyloxycarbonyl-4,6-dimethyl-2-mercaptopyrimidine in 1,4-dioxane is slowly added dropwise to this solution over a period of about 2 hours at room temperature, and the mixture is stirred for about 20 hours. This produces a whitish yellow precipitate which is removed by filtration. The precipitate is washed with 1,4-dioxane, combined with the 1,4-dioxane filtrate and subjected to distillation under reduced pressure to obtain a yellow oily substance. This is transferred to a beaker, water is added producing cloudiness which is filtered off, NaCl is added thereto and extraction is performed with ethyl acetate, and then the separated organic phase is dried over $K_2CO_3$. This is filtered and the solvent is distilled off under reduced pressure to obtain the target substance as a yellow oil.

Step II

The compound obtained in Step I is heated together with naphthalene-1,4,5,8-tetracarboxylic dianhydride in THF at 90° C. for 12 hours. After cooling to room temperature, the THF is distilled off under reduced pressure using an evaporator. Chloroform is added to dissolve the oily substance, and the insoluble portion is filtered off. Distilling off the filtrate under reduced pressure gives a light brown oily substance which is dissolved in methanol, and then water is added for reprecipitation. After suction filtration, vacuum drying is performed to obtain the target substance as a light brown substance.

Step III

TFA is added to the compound obtained in Step II, and the mixture is stirred at room temperature for 3 hours. Distilling off the TFA under reduced pressure gives a reddish brown oily substance. This is dissolved in methanol, and then chloroform is added for reprecipitation. The deposited precipitate is subjected to suction filtration and then drying under reduced pressure to obtain a peach-colored powdery compound.

Step IV

The compound obtained in Step III is dissolved in chloroform and then stirred together with BHHCT and triethylamine for 5 hours at room temperature. After completion of the reaction, the solvent is distilled off under reduced pressure to obtain a light brown oily substance. Upon adding purified water thereto and vigorously stirring, a light tan solid precipitates out, and this is filtered and then washed with ether to obtain the target substance.

The detecting method of the invention is characterized by using the detecting reagent of the invention, and fluorescent analysis is utilized for the detection.

Specifically, the detecting method of the invention preferably comprises the following steps. (1) Probe nucleic acid is immobilized on a solid surface, and target nucleic acid is added thereto for hybridization; (2) an intercalator is added; (3) washing is performed whereby the intercalator intercalated into the double strands remains and the non-intercalated substances and the substances non-specifically adsorbed to the probe or target nucleic acid are removed; (4) lanthanoid ion is added to the remaining intercalator to form a complex; and (5) time-resolved fluorescent measurement is employed to quantify the double-stranded nucleic acid.

The solid surface material used for immobilization of the probe may be selected from among ordinary publicly known materials. Specifically there may be mentioned glass, plastics, metals and the like. The carrier bearing the solid surface need not be flat, and may be in the form of beads, fibers or the like.

Examples of the invention will now be explained.

EXAMPLE

A synthesis example for the intercalator is illustrated below as Scheme 1.

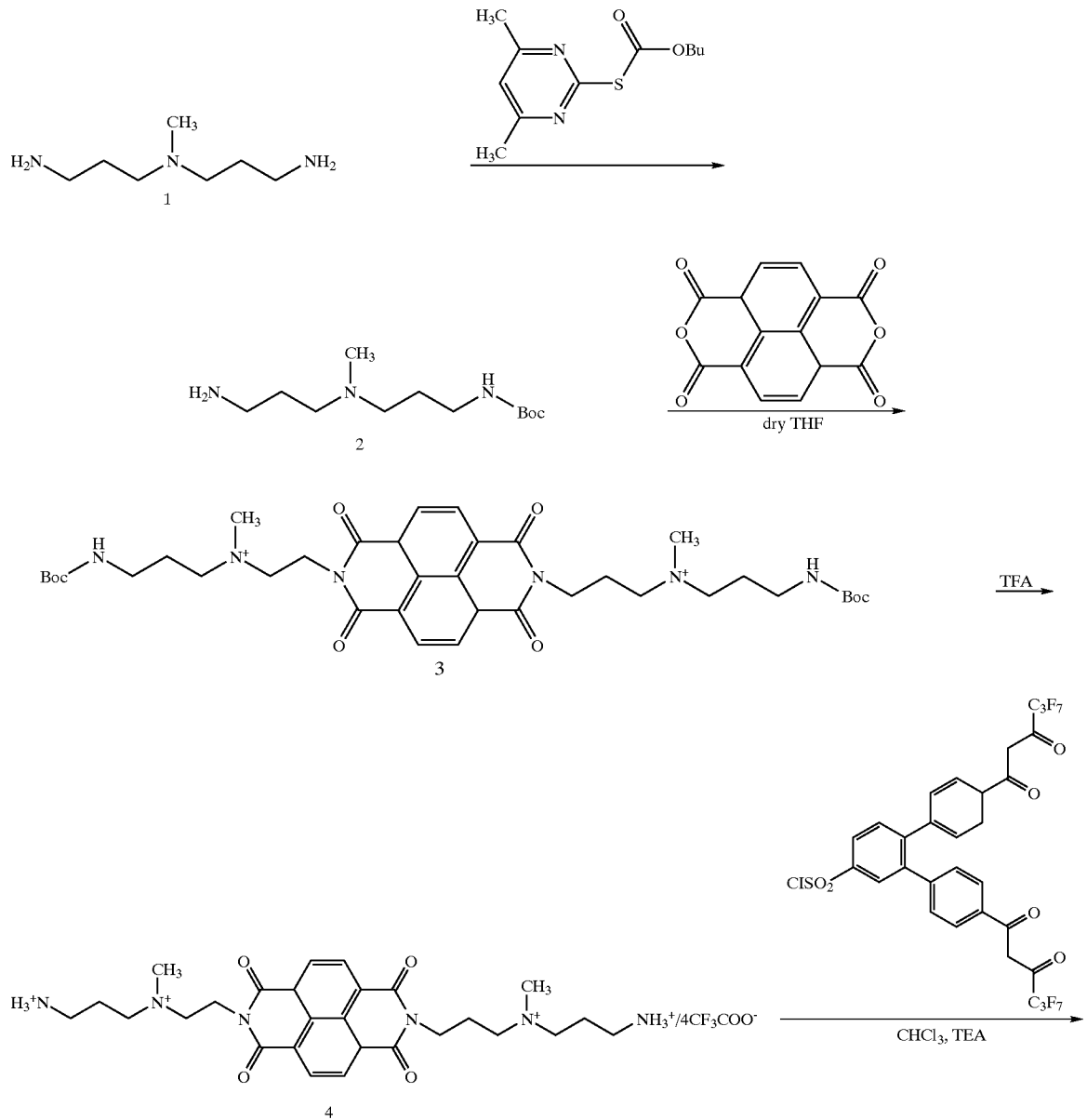

-continued

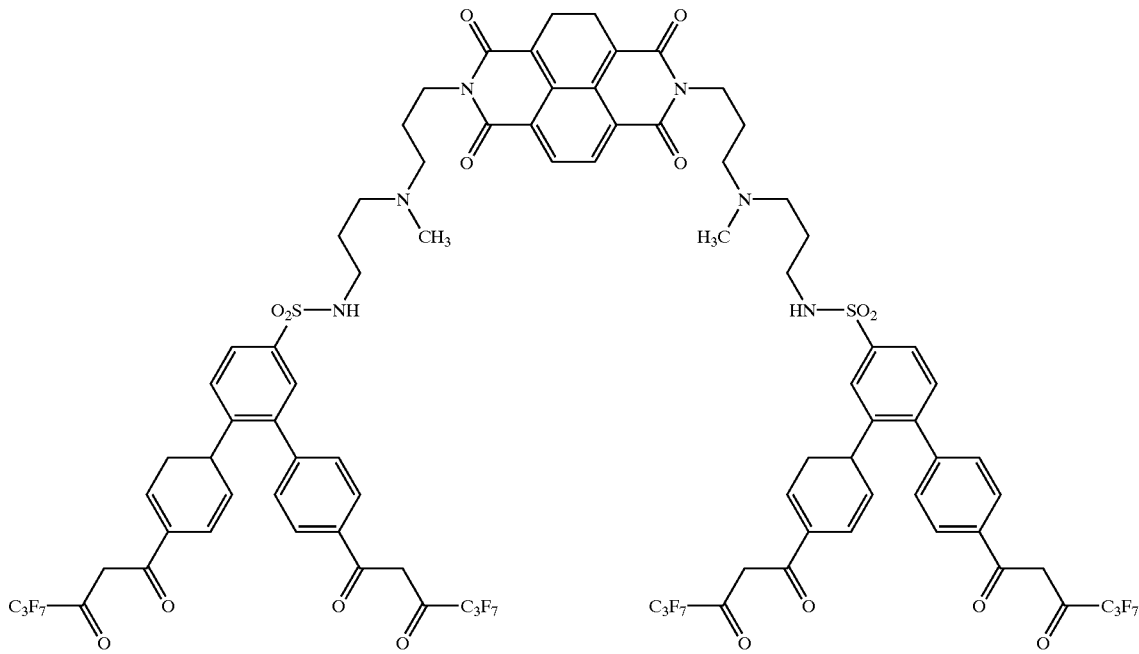

After dissolving 16.1 ml (0.1 mol) of N,N-bis(3-aminopropyl)methylamine in 45 ml of 1,4-dioxane, a solution of 12 g (0.05 mol) of S-tert-butyloxycarbonyl-4,6-dimethyl-2-mercaptopyrimidine in 50 ml of 1,4-dioxane was slowly added dropwise to the solution over a period of about 2 hours at room temperature, and the mixture was stirred for about 20 hours. This produced a whitish yellow precipitate which was removed by filtration. The precipitate was washed with 1,4-dioxane, combined with the 1,4-dioxane filtrate and subjected to distillation under reduced pressure to obtain a yellow oily substance. This was transferred to a beaker and 75 ml of water was added, producing cloudiness. After filtration, approximately 20 g of NaCl was added and extraction (50 ml ×4) was performed with ethyl acetate, after which the separated organic phase was dried over $K_2CO_3$. This was filtered and the solvent was distilled off under reduced pressure to obtain the target substance as a yellow oil. Weight: 8.0 g, yield: 66%, property: yellow oil (Compound 2).

After adding 1.67 g (6.23 mmol) of naphthalene-1,4,5,8-tetracarboxylic dianhydride, 25 ml of THF and 7.76 g (31.6 mmol) of compound 2, the mixture was heated at 90° C. for 12 hours. It was then cooled to room temperature, and the THF was distilled off under reduced pressure using an evaporator. Chloroform was added to dissolve the oily substance, and the insoluble portion was filtered off. Distilling off the filtrate under reduced pressure gave a light brown oily substance which was dissolved in 20 ml of methanol, and then 200 ml of water was added for reprecipitation. After suction filtration, vacuum drying was performed to obtain the light brown target substance. Weight: 3.82 g, yield: 85%, property: light brown powder, melting point: 113–117° C. (Compound 3).

After adding 5.35 ml of TFA to 1.00 g (1.38 mmol) of compound 3, the mixture was stirred at room temperature for 3 hours. Distilling off the TFA under reduced pressure gave a reddish brown oily substance. This was dissolved in approximately 15 ml of methanol, and then approximately 200 ml of chloroform was added for reprecipitation. The deposited precipitate was subjected to suction filtration and then drying under reduced pressure to obtain a peach-colored powdery compound. Weight: 1.28 g, yield: 95%, property: light peach powder (Compound 4).

After adding 0.34 g (0.35 mmol) of compound 4, 0.63 g (0.78 mmol) of BHHCT and 0.5 ml (3.5 mmol) of triethylamine to 5 ml of chloroform, the mixture was stirred for 5 hours at room temperature. After completion of the reaction, the solvent was distilled off under reduced pressure to obtain a light brown oily substance. Upon adding purified water thereto and vigorously stirring, a light tan solid precipitated out, and this was filtered and then washed with ether. Weight: 0.6 g, yield: 83%, property: light tan powder, melting point: >300° C., TOF-MASS: peak at 2064.27 (calculated: 2059.61). The NMR spectral absorption pattern data are shown in Table 1.

TABLE 1

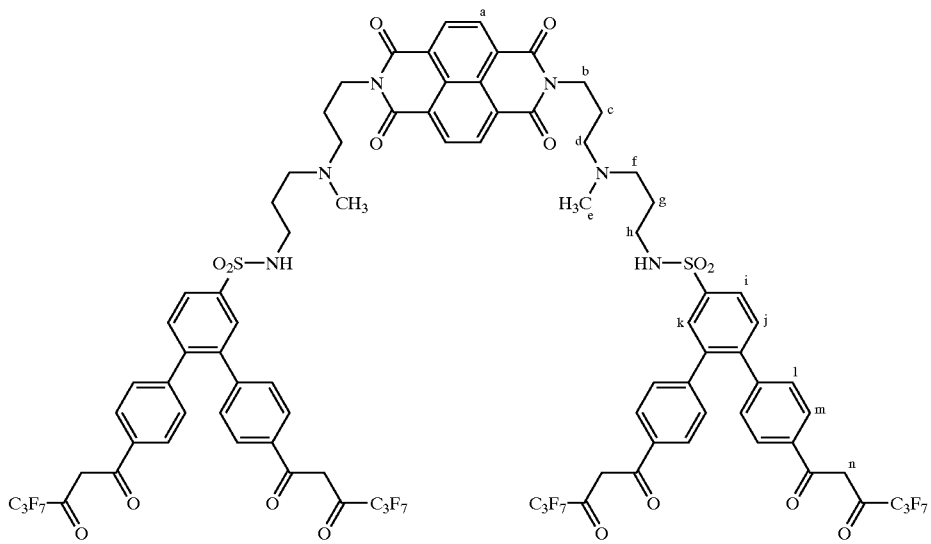

| δ (ppm) | Assignment | Splitting | Integral ratio |
|---|---|---|---|
| 8.70 | a | s | 3.9/4H |
| 8.05 | m | d | 5.0/8H |
| 8.00 | i | d | 4.3/2H |
| 7.88 | k | s | 3.1/2H |
| 7.80 | j | d | 2.8/2H |
| 7.38 | l | d | 6.5/8H |
| 6.99 | n | s | 2.5/8H |
| 4.14 | b | br | 3.4/4H |
| 3.17 | d, f | br | 11.1/8H |
| 2.91 | h | br | 3.9/4H |
| 2.76 | e | s | 7.3/6H |
| 2.09 | c | br | 4.1/4H |
| 1.86 | g | br | 3.1/4H |

Hybridization Experiment Using Assay Plate

A 5'-biotin labeled and 3'-FITC labeled synthetic oligodeoxyribonucleotide (23–24 mer; SEQ. ID. No. 1 and No. 2 of the Sequence Listing) was dissolved in SSPE buffer solution (100 mM phosphate pH 7.4, 149 mM NaCl, 1 mM EDTA), and the solution was dispensed into an avidin-coated assay plate (Delfia Streptavidin Microtitration Strips, C122-105) at various concentrations, and allowed to stand at room temperature for 10 minutes. After washing the plate with SSPE buffer solution, the number of DNA molecules remaining in the plate was quantified by FITC fluorescent measurement (Wallac ARVOSX 1420 Multilabel Counter). As a result, a maximum of 1.8 pmol of DNA molecules was found to be adsorbed to each well.

5'-biotin labeled DNA (SEQ. ID. No. 3 of the Sequence Listing) was dispensed into an assay plate and allowed to stand at room temperature for 10 minutes, and was then washed with SSPE buffer solution. Next, 100 pmol of 5'-FITC (FITC: fluorescein isothiocyanate) labeled DNA having the base sequence complementary to this DNA (SEQ. ID. No. 4 of the Sequence Listing) was added, and after heating at 85° C. for 10 minutes in SSPE buffer solution, it was incubated overnight at 45° C. After returning the plate to room temperature and washing, it was subjected to FITC fluorescence measurement. A similar simultaneous experiment was conducted using DNA which was non-complementary for the DNA on the plate (SEQ. ID. No. 1 of the Sequence Listing). As a result, significant FITC fluorescence was observed only when base pairs were formed. The excess non-hybridized DNA was thoroughly washed out by washing three times.

A 5'-biotin labeled DNA probe (24 mer) was dispensed into an assay plate, allowed to stand at room temperature for 10 minutes in SSC buffer solution, and then washed. Next, 100 pmol of 5-FITC labeled target DNA (24 mer) having the base sequence complementary to this DNA was added, and after heating at 85° C. for 10 minutes in SSC buffer solution, it was incubated overnight at 45° C. After returning the plate to room temperature and washing with SSC buffer solution, it was subjected to FITC fluorescence measurement to confirm that sufficient hybridization had occurred. After then adding 100 pmol of an intercalator-Eu complex (BHHCT:Eu=1:2) and allowing the mixture to stand in SSC at room temperature for 2 hours, it was washed twice with SSC buffer solution. Time-resolved fluorescent measurement was used to quantify the Eu complex remaining in the plate. The same experiment was also carried out for (ii) a sample with no probe DNA added and (iii) a sample in which the probe DNA and target DNA were non-complementary sequences. As a result, significant fluorescent intensity was measured only when hybridization occurred.

A 149 mer (SEQ. ID. No. 5 of the Sequence Listing) prepared using a 5'-biotin labeled primer and 3'-FITC labeled primer and double-stranded DNA composed of DNA complementary thereto were dispensed into an avidin-coated assay plate, and after standing at room temperature for 2 hours in SSC buffer solution for adsorption, the mixture was washed. A fixed amount of the complex was then added, and after standing at room temperature for 2 hours, the mixture was washed with SSC buffer solution. The number of intercalated complex molecules was quantified by time-resolved fluorescent measurement of the Eu. It was found as a result that the Eu fluorescent intensity and the number of immobilized DNA molecules were roughly proportional. This demonstrated that a constant base pair-:complex molecule number ratio is maintained when the complex binds to different numbers of DNA molecules on a plate.

Effect of the Invention

The detecting reagent for double-stranded nucleic acid according to the invention is characterized by comprising, in the same molecule, a naphthalenediimide skeleton as a group which is intercalatable into double-stranded nucleic acid, and a β-diketone group having a specific structure rendering it capable of forming a lanthanoid metal complex. Thus, the double-stranded nucleic acid detecting method of the invention allows quantification of nucleic acid samples with various abundance ratios since absolutely no modification (labeling) is carried out on the target nucleic acid, etc. used for the experiment.

In particular, the method allows quantification of nucleic acid molecule numbers or quantification of nucleic acid molecule lengths, which has been impossible in principle with conventional competitive hybridization, and thus permits greater quantification in analysis of gene expression.

What is claimed is:

1. A detecting reagent for double-stranded nucleic acid, comprising a naphthalenediimide group which is intercalatable into double-stranded nucleic acid and a β-diketone group capable of forming a lanthanoid metal complex said detecting reagent having the following formula (1) or (2):

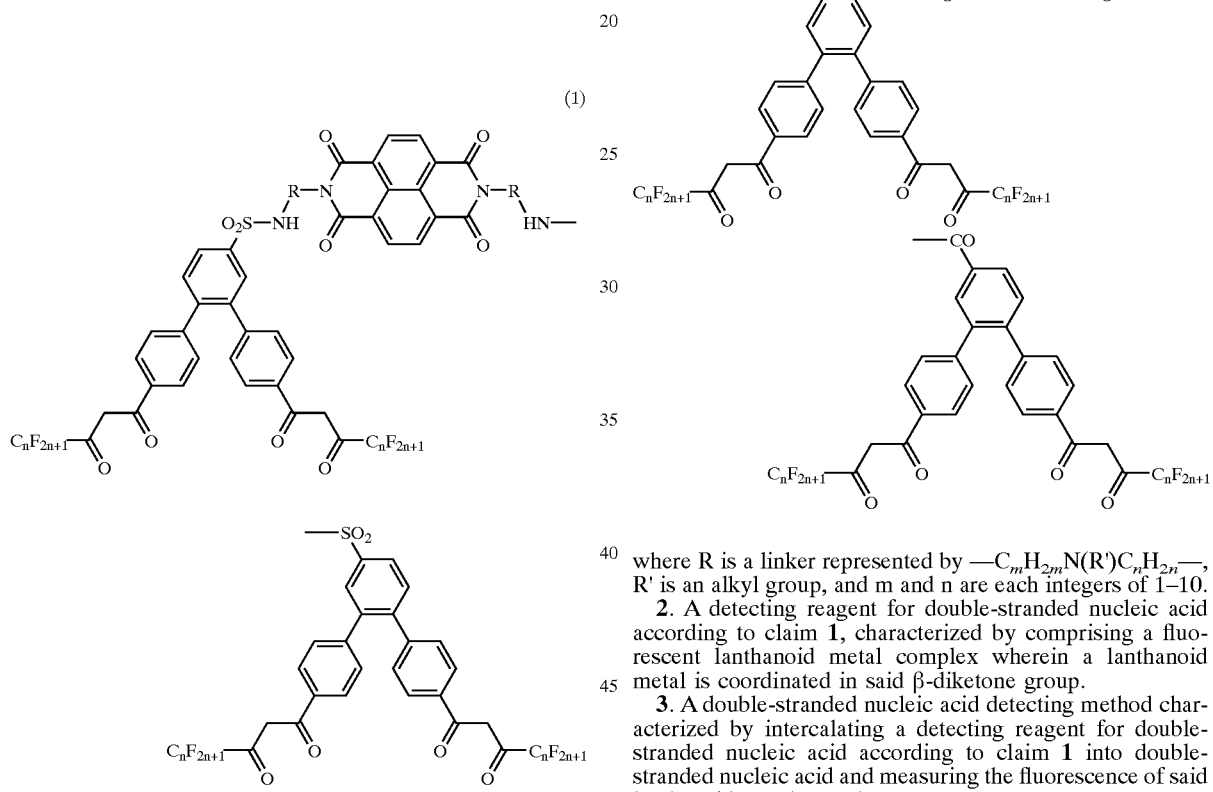

where R is a linker represented by $-C_mH_{2m}N(R')C_nH_{2n}-$, R' is an alkyl group, and m and n are each integers of 1–10.

2. A detecting reagent for double-stranded nucleic acid according to claim 1, characterized by comprising a fluorescent lanthanoid metal complex wherein a lanthanoid metal is coordinated in said β-diketone group.

3. A double-stranded nucleic acid detecting method characterized by intercalating a detecting reagent for double-stranded nucleic acid according to claim 1 into double-stranded nucleic acid and measuring the fluorescence of said lanthanoid metal complex.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: probe

<400> SEQUENCE: 1
cgccagggtt ttcccagtca cga                                           23

<210> SEQ ID NO 2
<211> LENGTH: 24
<212> TYPE: DNA
<213> ORGANISM: Artificial Sequence
<220> FEATURE:
<223> OTHER INFORMATION: probe

<400> SEQUENCE: 2
agcggataac aatttcacac agga                                          24

<210> SEQ ID NO 3
<211> LENGTH: 24
<212> TYPE: DNA
<213> ORGANISM: Artificial Sequence
<220> FEATURE:
<223> OTHER INFORMATION: probe

<400> SEQUENCE: 3
agcggataac aatttcacac agga                                          24

<210> SEQ ID NO 4
<211> LENGTH: 24
<212> TYPE: DNA
<213> ORGANISM: Artificial Sequence
<220> FEATURE:
<223> OTHER INFORMATION: probe

<400> SEQUENCE: 4
tcctgtgtga aattgttatc cgct                                          24

<210> SEQ ID NO 5
<211> LENGTH: 149
<212> TYPE: DNA
<213> ORGANISM: Artificial Sequence
<220> FEATURE:
<223> OTHER INFORMATION: probe
```

```
<400> SEQUENCE: 5
cgccagggtt ttcccagtca cgacgttgta aaacgacggc cagtgaattc gagctcggta      60
cccggggatc ctctagagtc gacctgcagg catgcaagct tggcgtaatc atggtcatag     120
ctgtttcctg tgtgaaattg ttatccgct                                       149
```